US009228154B2

(12) United States Patent
Tao et al.

(10) Patent No.: US 9,228,154 B2
(45) Date of Patent: *Jan. 5, 2016

(54) METHOD OF LOWERING THE CLOUD POINT OF FATTY ACID ESTERS

(71) Applicant: Purdue Research Foundation, West Lafayette, IN (US)

(72) Inventors: Bernard Y. Tao, Lafayette, IN (US); Samia Mohtar, Doha (QA)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/091,565

(22) Filed: Nov. 27, 2013

(65) Prior Publication Data

US 2014/0081037 A1 Mar. 20, 2014

Related U.S. Application Data

(63) Continuation of application No. 13/464,731, filed on May 4, 2012, now Pat. No. 8,598,379, and a continuation of application No. PCT/US2010/055464, filed on Nov. 4, 2010.

(60) Provisional application No. 61/258,434, filed on Nov. 5, 2009.

(51) Int. Cl.
*C11B 7/00* (2006.01)
*C11C 1/08* (2006.01)
*C07C 67/60* (2006.01)

(Continued)

(52) U.S. Cl.
CPC . *C11C 1/08* (2013.01); *C07C 67/60* (2013.01); *C11C 1/005* (2013.01); *C11C 3/003* (2013.01); *Y02E 50/13* (2013.01)

(58) Field of Classification Search
CPC .......... C11C 1/007; C11C 1/08; C07C 51/42; C07C 51/487; C07C 67/60
USPC ........................................................ 554/186
See application file for complete search history.

(56) References Cited

U.S. PATENT DOCUMENTS 2,596,344 A 5/1952 Newey et al.
2,653,122 A 9/1953 Arnold et al.

(Continued)

OTHER PUBLICATIONS

Bi, Yanlan, "Low-melting-point biodiesel derived from corn oil via urea complexation," Bioresource Technology 101 (2010) 12201226.

(Continued)

*Primary Examiner* — Deborah D Carr
(74) *Attorney, Agent, or Firm* — Bose McKinney & Evans LLP

(57) ABSTRACT

The present invention provides a robust and efficient process for reducing the cloud point of biodiesel fuel in which clathrates are formed from saturated fatty acid components as solvent is evaporated from a mixture of urea, methanol and fatty acid esters. The process speed can be fast, and is governed by the speed with which urea can be brought into clathrate forming contact with the fatty acid esters in the first instance, and then by the speed that solvent can be evaporated. Advantageously, substantially all of the solvent can be evaporated as pure solvent, which enhances process efficiencies and reduces cost. Additionally, substantially all of the urea can be used to form clathrates, further maximizing process efficiency.

21 Claims, 5 Drawing Sheets

(51) Int. Cl.
*C11C 1/00* (2006.01)
*C11C 3/00* (2006.01)

(56) References Cited

U.S. PATENT DOCUMENTS

| | | |
|---|---|---|
| 2,700,036 A | 1/1955 | Bradley et al. |
| 2,838,480 A | 6/1958 | Swern et al. |
| 2,853,478 A | 9/1958 | Stein et al. |
| 4,377,526 A | 3/1983 | Fujita et al. |
| 4,776,984 A | 10/1988 | Traitler et al. |
| 5,078,920 A | 1/1992 | Maza |
| 5,243,046 A | 9/1993 | Traitler et al. |
| 5,347,023 A | 9/1994 | Heynen et al. |
| 5,734,071 A | 3/1998 | Fex et al. |
| 6,395,778 B1 | 5/2002 | Luthria |
| 6,528,669 B1 | 3/2003 | Kulas et al. |
| 6,664,405 B2 | 12/2003 | Lee |
| 2002/0026063 A1* | 2/2002 | Luthria .................... 554/174 |
| 2005/0232956 A1 | 10/2005 | Bist et al. |
| 2006/0096159 A1 | 5/2006 | Bonsch et al. |
| 2009/0199462 A1* | 8/2009 | Bist et al. .................... 44/385 |

OTHER PUBLICATIONS

Dunn, R.O.; Shockley, M.W.; Bagby, M.O.; "Improving the Low-Temperature Properties of Alternative Diesel Fuels: Vegetable Oil-Derived methyl Esters," JAOCS, vol. 73, No. 12 (1996) 1719-1728.
Dunn, R.O.; Shockley, M.W.; Bagby, M.O.; "Winterized Methyl Esters from soybean Oil: An Alternative Diesel Fuel with Improved Low-Termperature Flow Properties," Society of Automotive Engineers, Inc., (1997) 640-649.
Harrington, K.J.; "Chemical and Phsical Properties of Vegetable Oil Esters and their Effect on Diesel Fuel Performance," Biomass 9 (1986) 1-17.

* cited by examiner

METHOD OF LOWERING THE CLOUD POINT OF FATTY ACID ESTERS

RELATED APPLICATIONS

This application is a continuation of U.S. patent application Ser. No. 13/464,731, filed May 4, 2012, which is a continuation of International Patent Application No. PCT/US2010/055464, filed Nov. 4, 2010, which claims priority to U.S. Provisional Patent Application No. 61/258,434, filed Nov. 5, 2009, all of which are hereby incorporated herein by reference in their entireties.

BACKGROUND OF THE DISCLOSURE

The present invention generally relates to fatty acid esters, and more particularly to a method for lowering cloud point of the fatty acid esters. A multitude of energy crises have been caused by disruption of fossil fuel supplies, coupled with significantly increased demand for fossil fuels by industrialized nations. In the past few decades, these crises have encouraged the development of alternative fuels. Additionally, since there are finite reserves of crude oil from which petroleum-based fuels are derived, there has also been a trend toward developing renewable fuels, such as biodiesel, which is derived from renewable sources.

Soy methyl ester (SME) or methyl soyate, the chemical description of which is provided below, is a common organic acid ester precursor for producing biodiesel. Organic acids, as the name indicates, are organic compounds with acid-like properties. One common group of organic acids are carboxylic acids, which have a "—COOH tail." Esters constitute a class of organic acid compounds where at least one —OH member is replaced by an alkoxy group (—O—$C_nH_{2n+1}$). In the case of methyl acetate ester, for example, a methoxy group (—O—$CH_3$), which is the simplest form of an alkoxy, has replaced the —OH group in acetic acid $CH_3COOH$. This results in $CH_3COOCH_3$, or methyl acetate ester. This chemical reaction is commonly termed esterification. Diagram 1, found below, shows the chemical bond structures for these compounds.

Diagram 1:

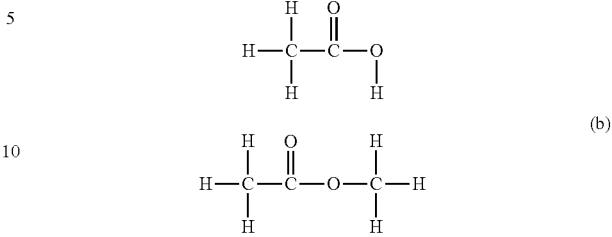

(a) Acetic acid; and (b) methyl acetate ester.

Fatty acids consist mainly of carbon chains and hydrogen atoms. These chains can be short with a small number of carbon atoms, e.g., butyric acid ($CH_3CH_2CH_2COOH$), or long with large number of carbon atoms, e.g., oleic acid $CH_3(CH_2)_7CH=CH(CH_2)_7COOH$. Fatty acids may include single and double bonds between carbon atoms. A saturated fatty acid has the maximum number of hydrogen atoms covalently bound to each carbon atom in the chain of carbon atoms, i.e., a saturated fatty acid has no double bonds. An unsaturated fatty acid has at least one double bond between two carbon atoms. Diagram 2, found below, shows an example of saturated and unsaturated fatty acids.

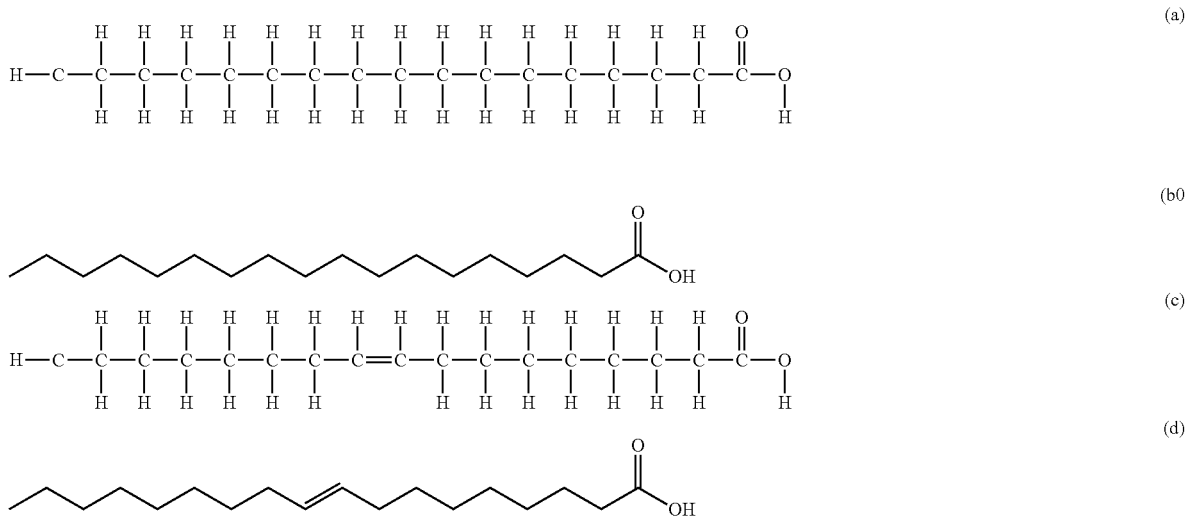

Diagram 2: (a) Chemical formula for palmitic acid; (b) chemical bond representation of (a); (c) chemical formula for palmitoleic acid; and (d) chemical bond representation for (c).

SME is produced by the transesterification of soybean oil with methanol in the presence of a catalyst. Transesterification results in a class of organic reactions where one ester is transformed into another ester by interchanging at least one alkoxy. The catalyst is often an acid or base. For example, methanol is added to NaOH and added to soybean oil to separate fatty acid esters from glycerin. In this example, the mixture of NaOH, methanol, and soybean oil is often heated to accelerate the esterification step.

SME profile by percent and by molecular weight is given in Table 1, below.

TABLE 1

Typical SME profile

| Fatty Acid Name | Carbon Design | Formula and Structure | Molecular Weight (g/mole) | Melting Point (° C.) | Percent of SME by Weight |
|---|---|---|---|---|---|
| methyl palmitate | C16:0 | $C_{15}H_{31}CO_2CH_3$ | 270.5 | 30.5 | 10.3 |
| methyl stearate | C18:0 | $C_{17}H_{35}CO_2CH_3$ | 298.5 | 39.1 | 4.7 |
| methyl oleate | C18:1 | $C_{17}H_{33}CO_2CH_3$ | 296.5 | −19.8 | 22.5 |
| methyl linoleate | C18:2 | $CH_3(CH_2)_4CH{=}CHCH_2CH{=}CH(CH_2)_7CO_2CH_3$ | 294.5 | −34.9 | 54.1 |
| methyl linoleate | C18:3 | $CH_3(CH_2CH{=}CH)_3(CH_2)_7CO_2CH_3$ | 292.5 | −57.0 | 8.3 |

Biodiesel produced by typical methods suffers from a crystallization phenomenon when temperatures decrease. Although this crystallization phenomenon is not limited to biodiesel, the temperature at which biodiesel begins to crystallize is substantially higher than petroleum-based diesel fuel. The crystallized constituents can clog fuel filters in vehicles using biodiesel and thereby cut off the fuel supply to the engine. The temperature at which solids begin to precipitate, thus producing a cloudy mixture, is referred to as cloud point (C.P.). Saturated fatty acid ester constituents crystallize at a higher temperature than unsaturated fatty acid esters. To lower the temperature at which crystallization occurs and thereby lower the C.P. of the fuel, several techniques can be used, examples of which include blending with petroleum-based diesel, introducing additives, and winterization. Winterization refers to crystallization and removal of saturated fatty acids, e.g., C16:0 and C18:0, and in some cases mono-unsaturated fatty acids, e.g., C18:1, that cause the biodiesel product to crystallize at an undesirably high temperature. The crystallization process is typically performed by cooling, and the removal process is typically performed by filtration of the crystallized particles of the saturated and in some cases mono-unsaturated fatty acids which leaves a mixture having a greater amount of polyunsaturated fatty acids compounds with lower C.P., thereby lowering the C.P. of the biodiesel so produced.

The winterization process has gained more interest in recent years. Winterization by itself produces low yields, i.e., a substantial portion of the starting material is lost during the filtration process. Therefore, use of compounds which improve the winterization process, typically referred to as "improvers," is essential. One process which includes the addition of improvers is referred to as fractionation, which uses the crystallization properties of esterified fatty acids to separate a mixture into low and high C.P. liquid fractions. During fractionation, these improvers create inclusion compounds/complexes. The process of creating an inclusion compound involves a host constituent, namely, the fatty acid molecule, which has a series of cavities or landing sites for attachment by a second chemical constituent, commonly referred to as the guest, which is an improver compound. The compound resulting from the combination of the host and the guest is called an "inclusion compound." The forces that hold the host and the guest constituents together are van der Waals type forces. That is, covalent bonds do not typically form between the guest and the host. Clathrates are one type of inclusion compound in which the spaces in the host constituent are enclosed on all sides, causing a "trapping effect."

A common improver compound is urea. Urea selectively forms clathrates with fatty acid molecules. Initially, urea forms clathrates with longer straight chain saturated fatty acid molecules, e.g., C18:0. As the number of longer chain saturated fatty molecules decline, urea then forms inclusion compounds with shorter straight chain saturated fatty acids molecules, e.g., C16:0, and then with mono-unsaturated fatty acid molecules that are nonlinear, e.g., C18:1. The reason for this selectivity is thought to be the ease of clathration observed with longer linear chain saturated fatty acids due perhaps to these moleuces possessing a larger number of landing sites for the urea molecule.

There are three different types of fractionation: dry fractionation, detergent fractionation, and solvent fractionation. Solvent fractionation has received a substantial amount of interest in recent years. The key to efficient fractionation is to thoroughly mix the improvers, e.g., urea, with the fatty acids. Solvent is used as a carrier for the improver. That is, the improver is dissolved in the solvent and the solvent-improver combination is added to the fatty acid to make a homogenous mixture.

Addition of solvent-improver to the fatty acid esters alone, however, does not promote formation of clathrates. For example, if urea is dissolved in methanol and the urea-methanol mixture is added to a mixture of fatty acid esters to form a homogenous mixture, urea molecules preferentially stay dissolved in methanol rather than forming clathrates with the fatty acid esters. In order to initiate the desired clathration, a change in conditions must occur. In the prior art, in order to begin the clathration, the homogenous mixture is cooled. As the homogenous mixture is cooled, urea molecules begin to form clathrates based on the selectivity described above. The clathrates crystallize and can be separated by filtration, centrifugation, etc. As the homogenous mixture is formed the temperature is often elevated. This is due to heating in the transesterification phase in order to accelerate the esterification step, and since the homogenous mixture is often formed directly after the transesterification phase. The desired C.P. is directly proportional to how much the homogenous mixture is cooled. For ultralow C.P.s, the target cooling temperature is very low. Thus, due to a thermodynamic equilibrium, clathration formation slows unless the temperature is further reduced. In order to form additional clathrates, the temperature must be further reduced.

However, clathration by cooling has several disadvantages. First, cooling the homogenous mixture is costly and in some cases not possible. For example, in many developing countries, the requirement to cool the homogenous mixture is prohibitively expensive due, for example, to high ambient temperature under some conditions. Second, cooling takes a substantial amount of time. Large batches of fatty acid esters have correspondingly large thermal masses. Therefore, an undesirably long time may be required to reach the target cooling temperature. Even if the homogenous mixture is allowed to naturally cool to room temperature, and thereby eliminate the need for active cooling, a substantial amount of time may be required due to the thermal mass. Also, relying on naturally cooling to ambient temperatures may result in inconsistent output quality because the target cooling temperature may vary and the target temperature plays a key major role in the final product's C.P. Third, in cooling based processes involving typical target temperatures, some urea almost invariably stays dissolved in the solvent instead of forming clathrates. To quantify how much urea is used, urea utilization is defined as a ratio of urea that forms clathrates to the total amount urea supplied in the process. In the cooling process, urea utilization is always inherently below 100%. Fourth, the cooling process requires eventual separation of methanol from the unsaturated-rich fatty acid esters. This is required for commercial biodiesel because of industry standards set for the final product which limit the amount of methanol in biodiesel, e.g., to 0.2% by volume.

What is needed is a robust, fast and efficient method of lowering the cloud point of Biodiesel that overcomes the drawbacks of the art discussed above.

SUMMARY

The present invention provides a robust and efficient process for reducing the cloud point of biodiesel fuel. In the inventive process, clathrates are formed from saturated fatty acid components as solvent is evaporated from a mixture of urea, methanol and fatty acid esters.

In one form thereof, the present invention provides a method of lowering the cloud point of fatty acid esters. In this method, fatty acid esters are provided, to which a solvent and urea are added. Substantially all of the solvent is evaporated, thereby forming clathrates mixed with liquid having less saturated fatty acid esters than the fatty acid esters initially provided. Substantially all of the clathrates are separated from the liquid; thereby, the liquid has a lower cloud point than the cloud point of the fatty acid esters initially provided.

Without wishing to be tied to any specific theory, it is thought that in the process taught herein, the solvent merely provides a delivery mechanism to facilitate contact between the urea and fatty acid esters. After facilitating this initial contact, the solvent can be removed quickly. It is believed that clathrate formation continues as solvent is removed from the mixture. That is, removing solvent effectively increases the concentration of urea in the mixture, which in turn maximizes the percentage of urea starting material that is used to form clathrates as compared to the cooling processes found in the prior art. This inventive process can remove substantially all of the solvent by evaporation (as pure solvent) early in the process and can also use substantially all of the urea to form clathrates. The resulting mixture of clathrates and low cloud point biodiesel can be separated by any of a variety of separation mechanisms.

Advantageously, the inventive process can proceed very fast, with substantially all of the urea forming inclusion complexes within minutes, as opposed to prior art processes which take hours and require large amounts of energy for cooling. It is believed that this advantageously fast formation of clathrates results from the inventive process being generally governed by equilibrium constraints rather than dynamic constraints. That is, process speed is largely governed in the first instance by the speed with which urea can be brought into "clathrate forming" contact with the fatty acid esters, and in the second instance the speed with which the solvent that facilitates the "clathrate forming" contact is removed. The faster these two process aspects are completed, the faster the overall process can be completed.

In this connection, it is generally preferable insofar as maximizing overall process speed to conduct the evaporation in a vessel in which the ratio of surface area to volume is maximized, which facilitates evaporation. On the other hand, the vessel selected should allow for adequate mixing of the urea, fatty acid esters and solvent to ensure sufficient clathrate forming contact opportunities between urea molecules and fatty acid esters.

One advantage of the process of the present invention is its speed. In contrast to prior art clathration by cooling processes, which require up to several hours for cooling, the inventive process can proceed essentially as quickly as clathrates can be formed and the solvent can then be evaporated.

As a related advantage, the process of the present invention does not require cooling and the concomitant costs associated therewith. Indeed, the inventive process can be employed at the tail end of a biodiesel manufacturing process, in which the temperature of the biodiesel is already elevated. Accordingly, the amount of energy needed to initially heat the solvent, urea and fatty acid esters, can thus be reduced.

Yet another advantage of the present invention is its efficient use of materials. Unlike prior art processes, e.g., clathration by cooling, in which approximately one third of the urea may be unused (because it remains in solution), processes embodying these teachings can utilize substantially all of the urea for clathration, such that having to process an undesirable urea-solvent by-product is largely avoided. In the same vein, processes embodying these teachings typically evaporate pure solvent that can be reused without further process steps to remove unwanted constituents, e.g., urea. This facilitates a process having a simple and efficient solvent recycle stream and an economy of process steps.

BRIEF DESCRIPTION OF DRAWINGS

The above-mentioned and other advantages of the present invention and the manner of obtaining them, will become more apparent and the invention itself will be better understood by reference to the following description of the embodiments of the invention taken in conjunction with the accompanying drawings, wherein.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

These teachings relate to lowering C.P. of fatty acid esters (hereinafter, "FAE") by an evaporative process which produces inclusion compounds mixed with refined liquid having a lower C.P. than the starting FAE material. An example of FAE is SME. A solvent is used as a carrier for the urea; i.e., the urea is dissolved in the solvent. As mentioned above, mixing urea/solvent with the FAE to generate a mixture in addition to changing at least one condition of the mixture promotes clathration. According to these teachings, evaporation of the solvent in which urea is dissolved is one change in the condition of the mixture that promotes formation of clathrates. As the solvent is allowed to evaporate, the urea begins to shift from a state in which it is dissolved in the solvent to a state in which it is part of an inclusion compound, or clathrate, with the FAE. In one embodiment, the clathrates are suspended solids in the FAE/urea/solvent mixture. The amount of solvent chosen is sufficient to dissolve the urea. The choice of how much urea should be added to the FAE is based on the desired C.P. depression. That is, according to the present teachings, lower C.P. values are achieved by adding more urea/solvent to the FAE, followed by evaporating the solvent.

Operation of diesel engines using renewable energy sources including triglycerides-derived fuels is known, as is the challenge of overcoming negative properties of these triglycerides-derived fuels, e.g., the gelling of bioderived diesel (biodiesel) at higher temperatures than petroleum derived fuels. The composition of typical un-winterized biodiesel from SME is as given in Table 2.

TABLE 2

Composition of SME based biodiesel

| Fatty Acid Ester | % by Weight |
| --- | --- |
| Methyl Palmitate (C 16:0) [1] | 10.3 |
| Methyl Sterate (C18:0) | 4.7 |
| Methyl Oleate (C18:1) | 22.5 |
| Methyl Linoleate (C 18:2) | 54.1 |
| Methyl Linolenate (C18:3) | 8.3 |

[1] The parenthetical reference (Cnn:n) indicates the number of carbon atoms of the molecule on the left side of the colon followed by the number of carbon - carbon double bonds in the molecule on the right hand side of the colon.

Figure 1:
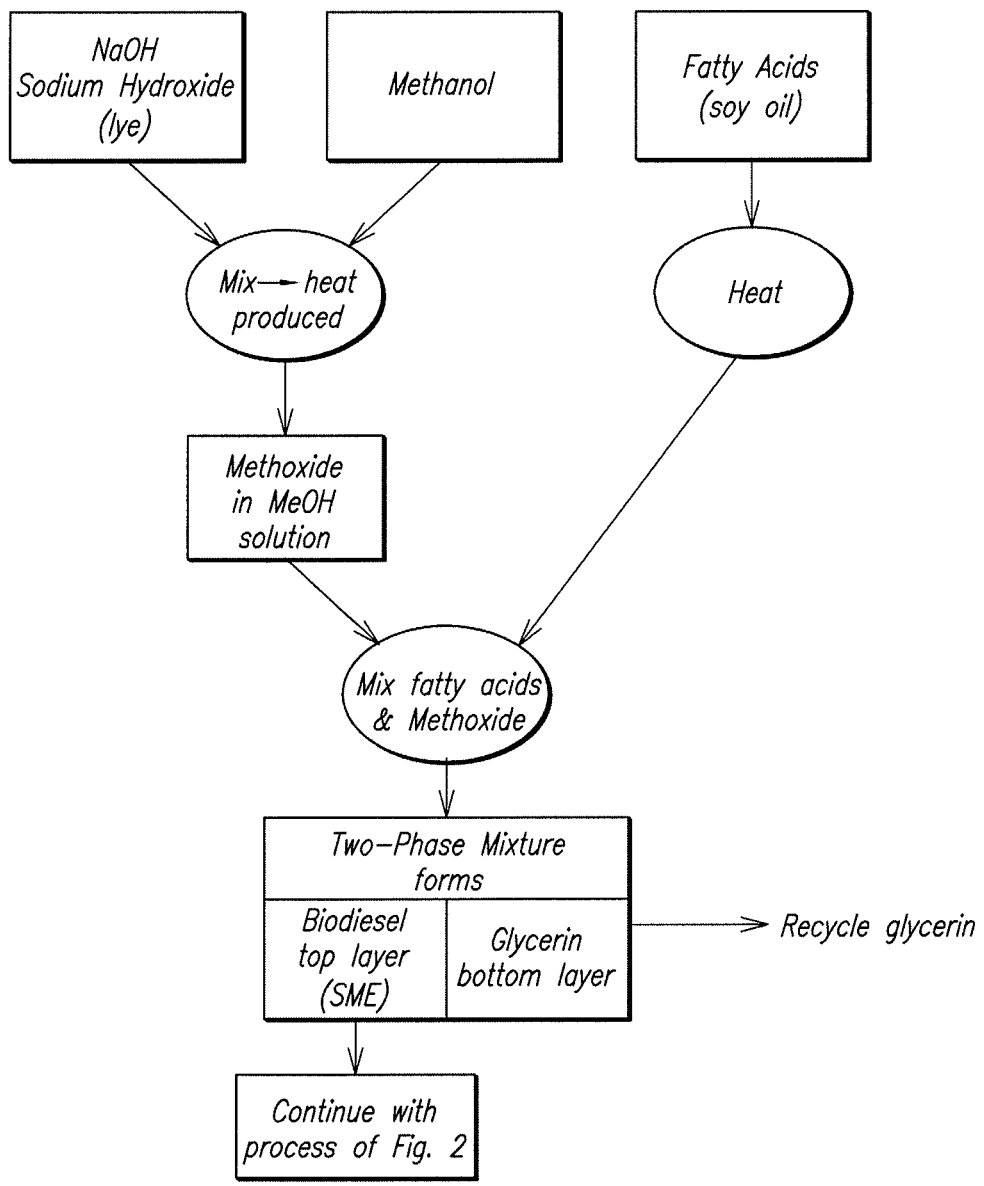
FIG. 1 is a schematic showing a transesterification process.

Referring to FIG. 1, transesterification of a starting material is shown. Transesterification reactants comprise a fatty acid source, e.g., soy oil, an alcohol, and a catalyst. Methanol is typically chosen as the reactant for SME transesterification, resulting in formation of the methyl ester from triglycerides. A hydroxide catalyst is typically used to accelerate the transesterification, although the reaction also responds to acid catalysis. Generally, mineral acids or mineral bases are selected as transesterification catalysts.

Typically, the transesterification of fatty acids from soy oil is considered "commercially complete" after a reaction time of from one to three hours at reaction conditions. Total time of reactants in the reaction vessel may exceed these times if it is necessary to heat reactants to reaction temperature in situ. In commercial settings, completion of the transesterification reaction occurs when continuation of the transesterification cannot economically be sustained. Commercial completion may be influenced by many factors some related to the equipment involved. Examples of these factors include capital cost/depreciation status, operating expense, size, geometry, separation equipment available, raw material cost, labor cost, or even the time of day as it relates to an operator's shift change.

The range of fat sources is not limited. Commercial fat sources generally include oilseeds, often locally produced, such as soybeans and canola. The carbon content of fatty acids from such sources ranges from 16 to 22 carbon atoms per fatty acid molecule.

In one embodiment, transesterification of raw materials of fats is most commonly accomplished by supplying fats and alcohol in a molar ratio of 1 mole fat (triglycerides) to 3 moles alcohol. Although the process is operable outside this ratio, unreacted raw materials may result. The reaction is observed to be nearly stoichiometric although it may be advantageous to add excess alcohol to the esterification step as will be discussed below. One percent catalyst by weight of fat is sufficient to facilitate the reaction at a commercially acceptable rate. Insufficient catalyst results in a slowed reaction; excess catalyst is not observed to significantly increase the reaction rate and may require additional separation effort at the completion of the reaction.

An example of the transesterification process is shown in FIG. 1. Sodium hydroxide (NaOH) is mixed with methanol, creating methoxide in methanol. The mixture produces heat. Fatty acids (in this case soy oil) are added to the methoxide mixture. The transesterification reaction generates glycerin and methyl esters. Following a period of quiescence, the glycerin phase will separate from the methyl esters at the completion of the transesterification, forming a liquid phase of methyl ester on top of a liquid phase of glycerin. The phases may then be separated by, e.g., decanting the methyl esters. Other phase separation methods such as a centrifugation may be used to accelerate and enhance the separation of glycerin from the methyl ester. The one exemplary technique for the above-described transesterification process is illustrated by the following example.

Transesterification of Soy Oil to Produce Un-Winterized SME Example:

Transesterification of soy oil with methanol in a vessel was completed with 6 molar parts methanol to 2 molar parts refined soy oil. NaOH as a catalyst at the rate of 1% by weight of soy oil was included. The liquid components were heated to 65° C. The condition was maintained for one hour with continuous mixing. The resulting two phases (upper layer—soybean methyl esters, methanol, impurities; bottom layer—glycerol, residual catalyst, impurities) were separated by decantation, using a 1000 ml separatory funnel. Analysis of the methyl ester phase disclosed the composition by weight in Table 3a.

TABLE 3a

Soy Oil Methyl Ester

| Fatty Acid Methyl Ester | % by Weight |
|---|---|
| Methyl Palmitate (C 16:0) [1] | 10.9 |
| Methyl Stearate (C18:0) | 4.1 |
| Methyl Oleate (C18:1) | 25.9 |
| Methyl Linoleate (C 18:2) | 53.0 |
| Methyl Linolenate (C 18:3) | 6.1 |
| Others | traces |
| Total Saturates | 15.0 |
| C.P. (° C.) | 3 |

For purpose of comparison, compositions of other vegetable oils are listed in Table 3b, while compositions of the fats of some land and marine animals are listed in Table 3c.

TABLE 3b*

Fatty Acid Composition of Some Vegetable Oils (%)

| Oil | C10:0 | C12:0 | C14:0 | C16:0 | C18:0 | C18:1 | C18:2 | C18:3 |
|---|---|---|---|---|---|---|---|---|
| Cocoa butter | | | | 26 | 3.5 | 37 | 2.5 | |
| Coconut | 7 | 48 | 17 | 8 | 3 | 6 | 2 | |
| Corn | | | | 11 | 3 | 27 | 57 | |
| Cottonseed | | | 0.8 | 25 | 2 | 18 | 53 | 0.1 |
| Olive | | | 1 | 15 | 2.6 | 67 | 13 | 1 |
| Palm | | | 1 | 46 | 5 | 39 | 9 | 0.4 |
| Palm kernel | 3.6 | 50 | 16 | 8 | 2 | 15 | 1 | |
| Peanut | | | | 10 | 3 | 52 | 29 | |
| Rapeseed | | | | 3 | 1 | 25 | 17 | 8.5 |
| Safflower | | | | 6 | 2 | 14 | 74 | 0.4 |
| Soybean | | | | 11 | 3.5 | 22 | 54 | 8 |
| Sunflower | | | | 7 | 4 | 17 | 71 | 0.2 |

TABLE 3c*

Fatty Acid Composition of Some Vegetable Oils (%)

| Oil | C4:0-12:0 | C14:0 | C16:0 | C18:0 | C18:1 | C18:2 | C18:3 | C20:5 | C22:6 |
|---|---|---|---|---|---|---|---|---|---|
| Beef tallow | | 3 | 26 | 22 | 42 | 2 | 0.2 | | |
| Butter | 12 | 10.8 | 26 | 10.3 | 28 | 2 | 1 | | |
| Chicken | | 0.9 | 22 | 10 | 41 | 20 | 2 | | |
| Lard | | 1.3 | 24 | 15.5 | 46 | 9 | 0.3 | | |
| Mackerel | | 6 | 16 | 3 | 15 | 2 | 1 | 5 | 9 |

*Source: Bailey Industrial Oil and Fat Products, 5th edition, 1996, Vol. 1, Edible Oil and Fat Products: General Applications, Y. H. Hui, editor Wiley Interscience, John Wiley and Sons, Inc.

A challenge posed by conventional biodiesel is its poor cold flow properties. The total content of saturates is a typical conventional biodiesel about 15% (wt/wt) for SME, see Table 3a, and causes the C.P. to be about 0° C. and pour point to be about −2° C. to −4° C. This limits the use of SME at low temperatures. Various efforts have been made to reduce or depress the C.P. of SME. A popular method for removal of saturated components is winterizing or cold filtering. Various studies have been conducted; however, these methods have very low yields for any significant reduction in the C.P.

These teachings disclose a C.P. reduction by a controlled removal of the saturated, and in some cases, mono-unsaturated fractions by a process involving evaporative clathration with continued filtration of clathrates rich in saturated and mono-unsaturated components. The process parameters of greater significance are: 1) FAE/urea/solvent (weight/weight/volume ratio), and 2) the amount of solvent that evaporates. The rate of evaporation appears to play an insignificant role in the formation of urea clathrates as long as the mixture of urea/FAE/alcohol is adequately mixed.

Figure 2:
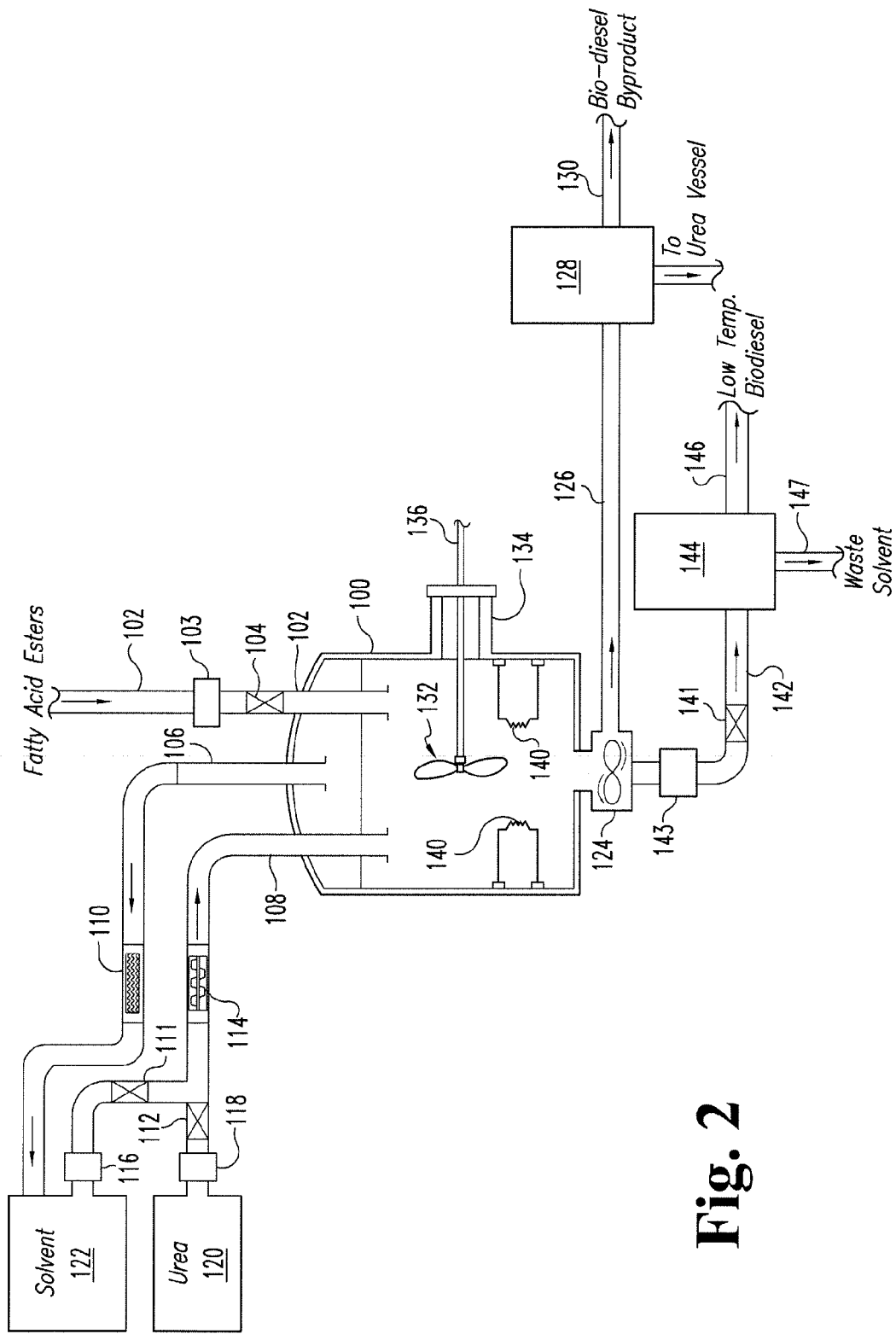
FIG. 2 is a schematic showing a first exemplary embodiment of evaporative clathration in accordance with the current teachings.

Referring to FIG. 2, one possible process for separating saturated and unsaturated fatty acid esters in accordance with the invention is shown. FAE, e.g., SME obtained from the transesterification process or from other sources and used as a starting material, is introduced into reactor 100. Reactor 100 can be in the form of a vessel or a conduit. The FAE starting material may already be at an elevated temperature, depending on whether the FAE is taken directly from the transesterification process where it is formed. To start the fractionation process, an amount of urea dissolved in a solvent, e.g., methanol is added to the FAE in reactor 100. A sufficient amount of solvent is used to dissolve the urea.

In one embodiment, once the volume of the FAE that is to be processed has been added to reactor 100, a corresponding amount of urea and solvent are also added to reactor 100. The ratio of FAE to urea determines the amount of clathration and subsequently the C.P. depression. As explained above, as the urea/solvent mixture is added to the FAE and the solvent is allowed to evaporate, urea begins to selectively clathrate with the FAE. For effective clathration, the mixture of urea/solvent and the FAE is continuously stirred or agitated. As will be described in greater detail below, solvent evaporation can be accomplished by several methods. Whatever method is used to evaporate the solvent, the starting material FAE should not reach its boiling condition. Depending on different starting material the FAE boils at different temperatures and pressures. In one embodiment the mixture of FAE/urea/and solvent is heated to about 60° C. to about 70° C. at atmospheric pressure. The clathration selectivity is such that urea preferentially begins to clathrate with C18:0, then with C16:0, and then with C18:1. If, however, there is sufficient urea present, clathration continues with C18:2, and then with C18:3. Solvent is evaporated by heating the FAE/urea/solvent mixture or by applying a vacuum to the mixture. Substantially all of the solvent is allowed to evaporate and substantially all of the urea is used to form clathrates. The compounds that form clathrates precipitate as solid particles that are suspended in the mixture.

FAE flows through pipe 102 and through valve 104 into reactor 100. Flow meter 103 and valve 104 are used to control the flow of FAE. In one embodiment, flow meter 103 provides an electrical signal to a controller which electrically controls valve 104. Flow of the FAE through pipe 102 may be by gravity or a pump (not shown).

Solvent vessel 122 and urea vessel 120 include solvent and urea, respectively. Flow meters 118 and 116 measure the flow of the urea and solvent. Valves 111 and 112 control the flow of the solvent and urea out of vessels 120 and 122. In one embodiment, flow meters 116 and 118 provide electrical signals to a controller, which in turn electrically controls valves 111 and 112. The flow of solvent and urea from vessels 122 and 120 may be by gravity or pumps (not shown). In one embodiment, a single vessel including a mixture of urea and solvent can replace the two vessels 122 and 120. In this embodiment, the mixture of urea and solvent should be continually agitated to maintain a homogenous mixture. Preferably, the ratio of urea to solvent should be such that the urea completely dissolves in the solvent. After the urea and solvent are brought together, they are thoroughly mixed by inline static mixer 114. In the single vessel embodiment inline mixer 114 may be avoided. The urea/solvent mixture flows through pipe 108 and into reactor 100 where it is mixed with FAE. As mentioned above, the flow of urea and solvent are monitored by flow meters 118 and 116 and the valves 112 and 111 are controlled so that the correct mixture of urea and solvent is achieved. The correct mixture is one where the urea can completely dissolve in the solvent.

The mixture of FAE/urea/solvent is agitated with mixer propeller 132 which is attached to shaft 136 held in housing 134. In one embodiment the FAE/urea/solvent mixture is heated by heating element 140. The mixture is heated to a temperature that causes evaporation of the solvent. The evaporated solvent flows through pipe 106. In one embodiment pipe 106 has sufficient length in a helical direction to allow condensation as a result of heat exchange with ambient air. In another embodiment, pipe 106 leads to condenser 110 where the evaporated solvent condenses to liquid. In another embodiment, pipe 106 is coupled to a vacuum unit (not shown) which produces a negative pressure in the space above the liquid in reactor 100, thereby aiding evaporation of the solvent. Alternatively, heater element 140 and the vacuum unit may be used together to further accelerate evaporation of the solvent. In any of the above cases, the condensed solvent may be recovered and reintroduced to solvent vessel 122 so that the solvent can be reused in the process.

As the solvent begins to evaporate, urea molecules begin to selectively form clathrates with FAE molecules. With substantially all of the solvent evaporated, the clathrates are in the form of solids suspended in FAE rich in unsaturated fatty acids (hereinafter "UFAE"). The UFAE flows through filter 124, valve 141, flow meter 143, and pipe 142. Filter 124 is used for separating clathrates in the form of suspended solids from the UFAE. This separation occurs only when valve 141 is opened. Filter 124 can be a continuous filter such that after the filter has collected sufficient clathrates, a new filter replaces the spent filter. An example of filter 124 is a liquid-solid separator rotary drum filter such as a Steadfast Equipment disposable rotary drum filter. In one embodiment, a measured reduction in flow of UFAE through flow meter 143 can be used as an indication to change the filter. In another embodiment (not shown in FIG. 2) the filter can be inside reactor 100. In this embodiment, filter 124 can be a continuous or rotary filter made up of a several filtering surfaces which collect the suspended clathrates as mixer propeller 132 agitates the FAE/urea/solvent mixture.

The UFAE exits reactor 100 by the force of gravity or actively by using a pump (not shown) or by applying a vacuum. In one embodiment, a controller receives an electrical signal from flow meter valve 143 and the controller electrically controls valve 141. Valve 141 is opened only when substantially all of the solvent has been evaporated. In order to determine how much of the solvent has been evaporated, one of several methods can be used. Examples of these methods are: 1) mass chromatography, 2) mass balance, 3) batch measurement using statistical process control, and 4) flash point testing using samples to determine an amount of solvent that remains in the UFAE by evaporating the solvent from the sample and measuring the flash point of the evaporated solvent.

In other embodiments, different separation techniques known to those skilled in the art can be used to separate the clathrates form the UFAE. Examples of these techniques, performed alone or in combination, are vacuum filtration, centrifugation, and solvent extraction. With some of these techniques a separation medium is used in combination with the technique. Also, in all of these techniques the separation step occurs after the evaporation step is completed. In the vacuum filtration case, a negative pressure is applied to the liquid extract, i.e., the UFAE, downstream from the separation medium. Application of vacuum accelerates the passage of the liquid extract through the separation medium. Alternatively, a positive pressure may be applied by air pump (not shown) to the interior head portion of reactor 100 to promote the passage of the liquid extract through the separation medium. This positive pressure will only be applied after the evaporation stage is completed to make sure no interference occurs with the evaporation process. In the centrifugation technique the liquid UFAE is separated from the clathrates by centrifuging these two components at speeds in the range of about 10,000 to about 14,000 rpm. The centrifugation process results in separation of the two components into liquids that can be separated by, e.g., decantation. In the solvent extraction technique, a filtration solvent such as hexane is used, in which urea does not dissolve. The solvent is applied to the UFAE to accelerate the extraction from the clathrates. A filtration solvent in which urea cannot dissolve should be used to avoid a reverse clathration process. The filtration solvent is added to the mixture of FAE and clathrates and the combination is filtered using a separation medium. Addition of the filtration solvent promotes passage of the UFAE through the separation medium.

The liquid that exits reactor 100 through pipe 142 is UFAE, and is substantially free of solvent and urea. The UFAE flows to residual solvent removal station 144. Although the goal is to evaporate and remove all of the solvent, traces of the solvent may be present in the UFAE. Substantially all of the initial urea, however, forms clathrates and zero to only trace amount of urea is present in the UFAE. The low C.P. output of the process shown in FIG. 2 cannot contain any significant amount of solvent (see ASTM D6751 which limits methanol content to 0.2% by volume). The residual solvent removal station 144 removes residual solvent. The low C.P. output flows out of pipe 146, while any solvent is removed through pipe 147. The removed solvent can be optionally processed and recycled into solvent vessel 122. In one embodiment, any residual solvent is evaporated and removed from the main UFAE. In another embodiment, the solvent is washed with hot acidified water, e.g., 60° C. and pH 3-4.

The filtered clathrates flow through pipe 126 to urea separation station 128. Different techniques may be used to break down the clathrates and separate the urea from the saturated-rich FAE (hereinafter SFAE). In one embodiment, the clathrates are heated from about 110 to about 120° C. in order to melt the urea from the SFAE, followed by separating the melted urea from the SFAE by, e.g., decantation. In another embodiment, the urea is washed from the SFAE by applying warm water, e.g., about 65° C., followed by separation of the SFAE and the washed urea. In this embodiment, urea is more soluble in water than in SFAE. Therefore, the urea separates from SFAE and forms a layer below the SFAE. The lower layer is removed and the urea is dried, and preferably ground before being recycled into the urea vessel. In yet another embodiment, the clathrates are mixed with a solvent in which urea cannot dissolve, e.g., hexane. Due to the insolubility of urea in the solvent, urea precipitates from the mixture of solvent and SFAE. The liquid layer above the urea containing SFAE and solvent is separated from the urea. The SFAE is separated from the solvent by evaporation or washing the solvent from the SFAE. In all of these embodiments, the separated SFAE is a byproduct that has many uses where it is desired to have a high gel point, e.g., candles.

The process shown in FIG. 2 can be modified so that urea/solvent is added in an incremental fashion. This alternative embodiment can prevent a clogging condition which is described as follows. If all of the necessary urea/solvent is added at once to the volume of FAE in reactor 100, as substantially all of the solvent evaporates, substantially all of the urea forms clathrates in the form of a large amount of suspended "slurry-like" solids. As valve 141 is opened to allow the UFAE to exit reactor 100, the suspended solids can quickly clog filter 124, resulting in a reduction or blockage of FAE flow through valve 141.

In order to overcome this clogging problem, the known volume of urea/solvent can be added to the FAE in increments. First, the amount of urea/solvent that is needed to achieve the desired C.P. is determined. Then, under the control of a controller, that amount of urea/solvent is divided into many increments and added to reactor 100. Filter 124 in this embodiment is a continuous internal filter, e.g., a liquid-solid separator rotary drum filter such as a Steadfast Equipment disposable rotary drum filter. As mentioned above, the FAE/urea/solvent mixture should be continuously mixed and agitated. As urea/solvent is incrementally added to reactor 100, conditions should be such that the solvent in which the urea is dissolved quickly evaporates upon introduction into reactor 100 causing quick clathration. A small amount of clathrates are formed with each increment of urea/solvent added to the FAE. Under these conditions, the continuous filter does not suffer from the same clogging issue. As the final increment of urea/solvent is added and the subsequent clathrate is filtered, valve 141 opens and the UFAE flows out of reactor 100. In this embodiment, filter 124 continuously filters the suspended clathrates while a scraper assembly separates the solids from the filter medium. The separated solids are transferred to urea separation station 128 for urea recovery and reuse.

Figure 3:
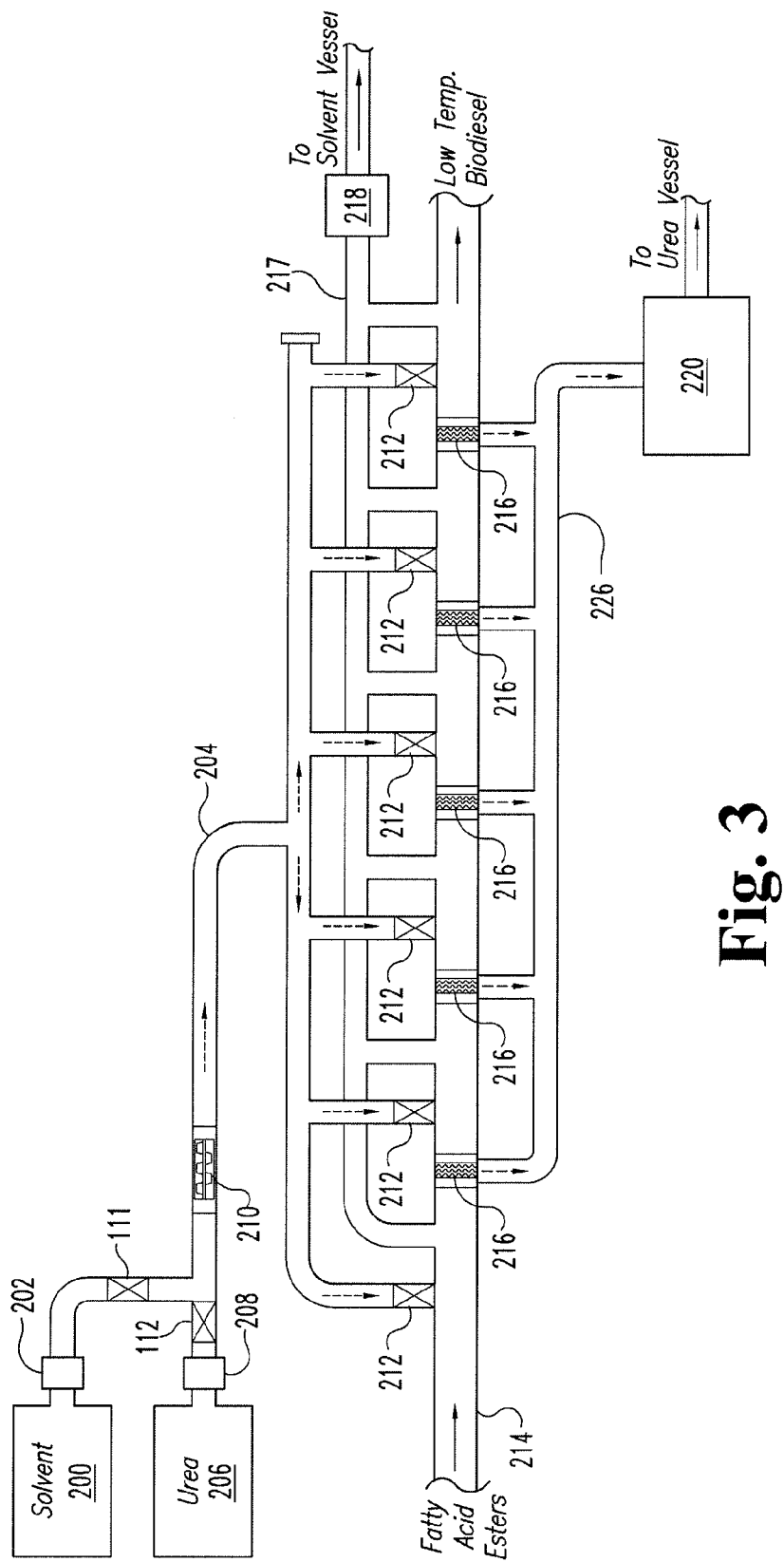
FIG. 3 is a schematic showing a second exemplary embodiment of evaporative clathration in accordance with the current teachings.

Another possible embodiment is shown in FIG. 3. In this embodiment, incremental amounts of urea/solvent are added in an inline, stepwise fashion to the FAE. Solvent vessel 200 and urea vessel 206 contain solvent and urea which are mixed by static inline mixer 210, and the mixture flows through several pipes 204. The flow of the solvent and the urea is examined and controlled by monitoring flow meters 202 and 208 and controlling valves 111 and 112. In one embodiment, flow meters 202 and 208 provide electrical signals to a controller which electrically controls valves 111 and 112. Flow of the solvent and urea from vessels 200 and 206 may be by gravity or by use of pumps, not shown. In one embodiment, a single vessel containing a mixture of urea and solvent can replace the two vessels 200 and 206. In this embodiment, the mixture of urea and solvent must be continually agitated to ensure a well mixed combination. Also, the ratio of urea to solvent must be such that the urea completely dissolves in the solvent. After the urea and solvent are brought together, the two are thoroughly mixed by inline, i.e., static, mixer 210. In the single vessel embodiment inline mixer 210 may be avoided. The urea/solvent mixture flows through pipe 204 and enter conduit 214 through valves 212, wherein the urea/solvent is mixed with FAE. As mentioned above, the flow of urea and solvent are monitored by flow meters 208 and 202 and the valves 112 and 111 are controlled so that the correct mixture of urea and solvent is achieved. The correct mixture is one where the urea can completely dissolve in the solvent.

Several valves 212 control introduction of urea/solvent into the flow of FAE flowing through conduit 214. The condition of conduit 214 is such that addition of urea/solvent at any point along conduit 214 causes immediate evaporation of the solvent through pipes 224. This can be accomplished by either applying a vacuum to conduit 214 or by heating conduit 214. The evaporated solvent flows through pipe 217 and condenser 218 and is recovered into solvent vessel 200. The evaporation of the solvent also causes immediate selective clathration of urea with FAE. The clathrates are collected on inline filters 216, such as a Steadfast Equipment disposable rotary drum filter which has an integrated scraping action which separates the clathrates from the filter medium. The clathrates are then transferred through pipes 226 to urea recovery station 220. In urea recovery station 220, the urea is separated from SFAE by any of the methods described above, e.g., disassociation by heating and thereby melting the urea, washing with warm water, and applying a solvent in which urea is not dissolvable. With all of these separation techniques the urea is recovered and reintroduced into the urea vessel 206. The SFAE is used as a byproduct that has many uses where it is desired to have a high gel point, e.g., candles.

Figure 4:
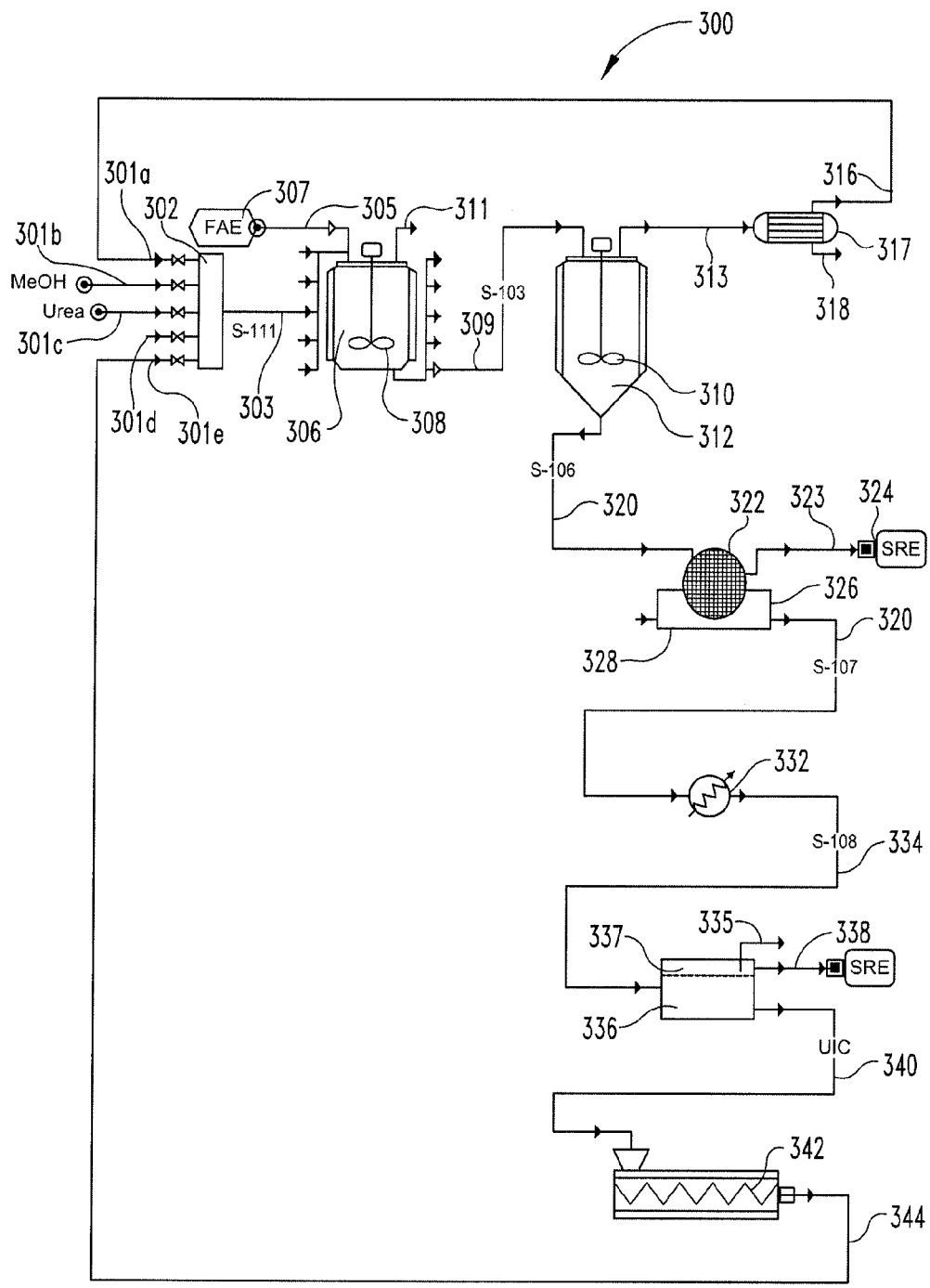
FIG. 4 is a schematic showing a third exemplary embodiment of evaporative clathration in accordance with the current teachings.

Referring now to FIG. 4, a diagrammatic representation of another embodiment of a batch evaporative urea fractionation process, suitable for practicing some of the embodiments of the invention is disclosed. Briefly, a pre-mixing vessel 302 is fitted with a series of valves (301a-e) and each valve is in turn connected to a source of at least one compound that can be pre-mixed, for example, methanol (MeOH), recycled MeOH, urea and recycled urea. Next, the pre-mixed materials formed via pre-mixing vessel 302 are fed via pipe 303 into a blending/storage tank 306 which is outfitted with a mixing means 308. Tank 306 is connected via pipe 305 to a source of FAE 307. After mixing, some of the contents of tank 306 are fed via pipe 309 into crystallization chamber 312 which is outfitted with a mixing means 310. The headspace in chamber 312 is connected to an exhaust pipe 313 which is in turn connected to vacuum source 317. Vacuum source 317 is outfitted with at least two liquid output pipes. Pipe 316 carries MeOH removed by vacuum from tank 310 back to mixing vessel 302. A second pipe 318 connected to vacuum source 317 carries condensates having a boiling point different from the boiling point of MeOH away from vacuum source 317. Pipe 318 may be plumbed to a waste receptacle or to a purification apparatus (not shown) for separation and/or fractionalization or additional processing of the contents of pipe 318.

Still referring to FIG. 4, after a holding time in vessel 312 intended to increase the level of clathrates produced in the process, a portion of the liquid content of vessel 312 is fed into pipe 320. Pipe 320 is also connected to a filtration device, for example, rotary vacuum filtration device 322. Solids such as clathrates form on the surface of filtration device 322. Liquid substantially free of clathrates such as cold flow-esters (CFE) flow though filtration device 322 and are transferred out of the system via pipe 324. Excess liquid and/or solid material from the surface of filtration device 322 may be re-applied to the surface of device 322 via re-circulation pipe 326. Material including both solids collected from the surface of filtration device 322 and liquids substantially free of CFE are fed by pipe 326 to a heat source such as 332. Liquid formed after heating by heating device 332 is transferred via pipe 334 to holding tank 336 which is vented via pipe 335. Vent pipe 335 may be connected to a filtration, condensation or separation unit (not show). Liquids that collect in tank 336 above flotation pipe 337 are siphoned out of holding tank 336 via pipe 338. This material is comprised primarily of saturate rich esters (SRE). The contents of tank 338 collecting in tank 336 below flotation line 337 are removed from tank 336 via pipe 340. The material in pipe 340, which includes urea inclusion compounds (UIC), is fed into extrusion device 342. The extrudate recovered from extrusion device 342 is highly enriched in urea and is transferred by pipe 344 to pre-mixing vessel 302.

Figure 5:
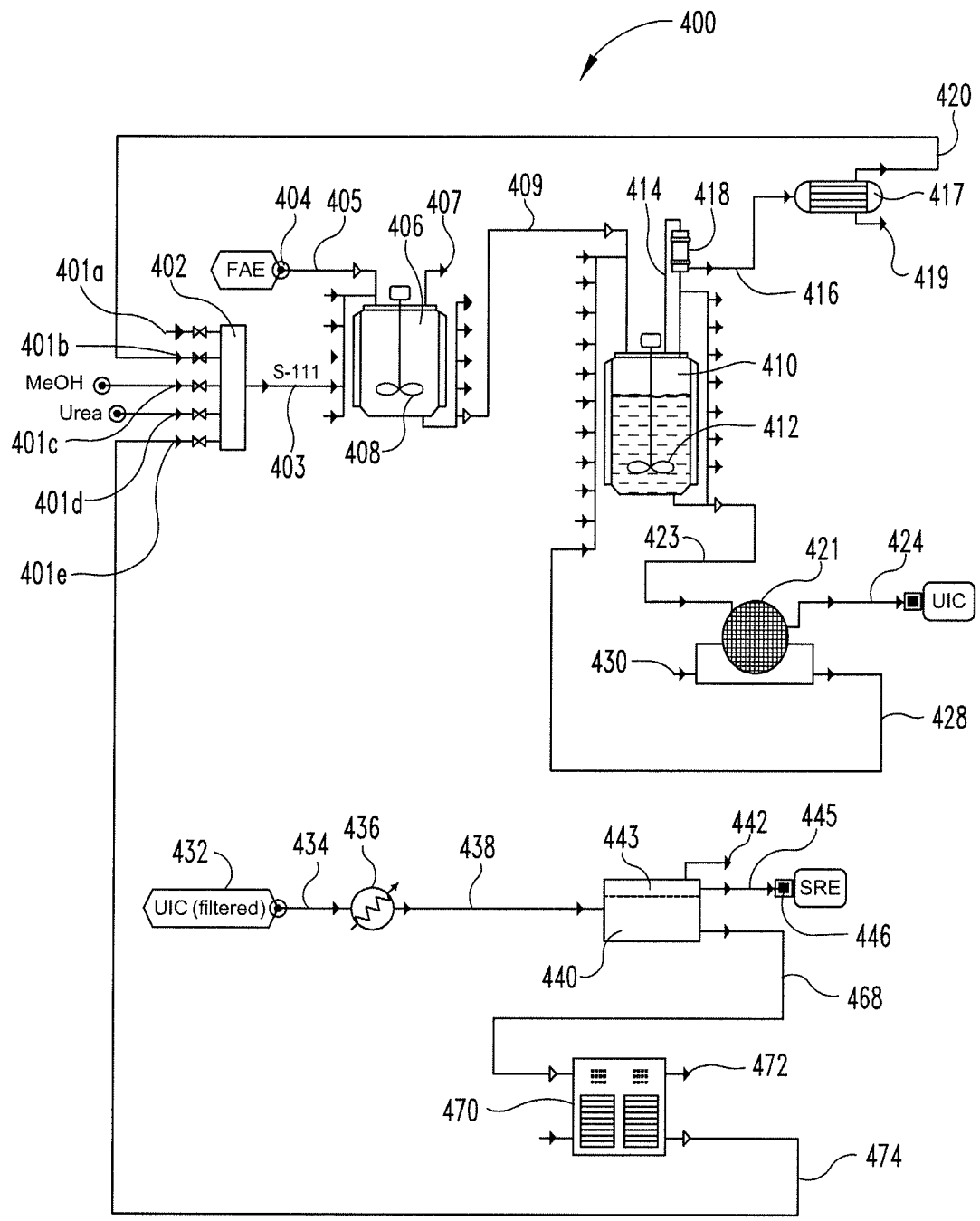
FIG. 5 is a schematic showing a forth exemplary embodiment of evaporative clathration in accordance with the current teachings.

Referring now to FIG. 5, a diagrammatic representation of a semi-continuous system suitable for practicing some of the embodiments of the invention is shown. Pre-mixing vessel 402 is fitted with a series of valves (401a-e). Each valve is in turn connected to a source of at least one compound that can be pre-mixed, for example, methanol (MeOH), re-cycled MeOH, urea and re-cycled urea before the pre-mixture is mixed with (FAE). Next, the pre-mixed material is fed into a blending/storage container 406 which is outfitted with a mixing means 408 and is also connected to a source of FAE. After mixing various components, including, for example, urea, methanol and FAE, a portion of the contents of container 406 is fed via pipe 409 (which is fitted to or near the bottom of tank 406) to a second tank 410 which includes mixing device 412. The head space of tank 410 is connected to pipe 414 which is in turn connected to a vacuum source 418. Alternatively, tank 410 may be heated (device not shown). Material is drawn from tank 410 by vacuum source 418 and is fed to condenser 417 via pipe 416. Methanol is collected from condensation unit 417 and is fed via recycle pipe 420 to mixing vessel 402. Material from condensation unit 417 that has a boiling point different from methanol is removed from condensation unit 417 via pipe 419. Pipe 419 may be connected to a waste receptacle or to another recovery and/or separation device (not shown). Liquid from tank 410 is fed via pipe 423 to a filtration device such as rotary vacuum filtration device 421. Liquids that pass through filtration device 421 are collected via pipe 428. These liquids are substantially comprised of cold-flow esters (CFE). Solid material that collects on the surface of filtration device 421 is enriched in urea inclusion compounds (UIC), including clathrates. This material is collected for additional processing including, for example, the dissociation of urea inclusion compounds to liberate urea from clathrates.

Still referring to FIG. 5, a tank 432 including filtered UIC collected from, for example, the surface of rotary filtration device 421 is heated to a temperature sufficient to dissociate the urea rich clathrates by heating device 436, which is connected to tank 432 via pipe 434. Melted material is fed via pipe 438 connecting heating device 436 to a settling tank 440. Settling tank 440 is outfitted with head space vent pipe 442 which may be connected to an additional condenser or separation device (not shown). Liquids in settling tank 440 above flotation line 443 are fed into pipe 445. This liquid is comprised substantially of saturate-rich esters (SRE) 446. Liquid collected in settling tank 440 below flotation line 443 is removed from tank 440 via pipe 468. Pipe 468 is in turn connected to a urea recovery device such as tray dryer 470. Vapor from tray dryer 470 is vented via pipe 472 while dried urea from tray dryer 440 is collected via evacuation outlet 474 and may be introduced into pre-mixing vessel 402.

These teachings provide numerous advantages over known prior art, for example, prior art processes in which clathration is promoted by cooling the mixture of FAE/urea/solvent. For example, substantially all of the urea is used in the clathration process. Since urea forms clathrates with SFAE, the remaining UFAE is substantially free of urea and need not be further processed to remove the urea. This means that smaller amounts of urea can be used for each batch of FAE as, for example, compared to clathration by cooling. Another advantage is that substantially all of the solvent is evaporated during the clathration process. Therefore, minimal processing is required to remove any traces of solvent that is left in the UFAE. Additionally, little or no solvent is wasted using the solvent recovery steps, described above. Also, evaporation of substantially all of the solvent makes it possible for substantially all of the urea to clathrate with SFAE. Yet another advantage is that no cooling is required once urea/solvent have been added to the FAE to promote clathration. Still another advantage is that since the clathration process according to these teachings is closely controlled, the yield of the low gel point output is higher than, for example, clathration by cooling.

Exemplary techniques are illustrated by the following examples. A summary of these examples is found in Table 4. In Table 4, FAE constituents are listed for each example. Additionally, resulting C.P., % by weight of starting FAE and the proportions of FAE to urea to solvent is listed for each example.

EXAMPLE 1

50 grams of Soy Methyl Esters and 25 g of urea were added to 125 ml of methanol. The mixture was heated to ~55° C., with constant stirring in a round bottom flask. After all components were dissolved, the flask was connected to a rotary evaporator and the methanol was evaporated applying ~20 in Hg of vacuum and a water bath at 60° C. 50 ml of hexane were added to the residual contents of the flask and the contents of the flask were shaken for 2-3 minutes and then transferred into a Buchner funnel. The hexane extract was recovered by vacuum filtration, transferred into a round bottom flask and connected to a rotary evaporator to flash off the hexane and thus recover the unsaturated-rich soy methyl esters. The yield was 69.1% of the initial SME mass. The FAE profile of the material before and after treatment is shown in Table 4.

TABLE 4

| Fatty acid methyl ester | Original SME Composition | Fractionated SME composition |
| --- | --- | --- |
| Methyl palmitate (C16:0) | 10.5% | 4.3% |
| Methyl Stearate (C18:0) | 5.7% | 1.4% |
| Methyl Oleate (C18:1) | 25.8% | 24.9% |
| Methyl Linoleate (C18:2) | 49.7% | 60.8% |
| Methyl Linolenate (C18:3) | 8.3% | 8.6% |
| Others (>C20) | Traces | 0 |
| Total saturated fatty acids | 16.2% | 5.7% |

The cloud point of the fractionated SME was −18° C.

EXAMPLE 2

20 grams of Soy Methyl Esters and 18 g of urea were added to 80 ml of methanol. The mixture was heated to ~65° C., with constant stirring in a round bottom flask. After all components were dissolved, the flask was connected to a rotary evaporator and the methanol was evaporated applying ~20 in Hg of vacuum and a water bath at 60° C. 50 ml of hexane were added to the residual contents of the flask and the contents of the flask were shaken for 2-3 minutes and then transferred into a Buchner funnel. The hexane extract was recovered by vacuum filtration, transferred into a round bottom flask and connected to a rotary evaporator to flash off the hexane and thus recover the unsaturate-rich soy methyl esters. The yield was 63.3% of the initial SME mass. The FAE profile of the material before and after treatment is shown in Table 5.

TABLE 5

| Fatty acid methyl ester | Original SME Composition | Fractionated SME composition |
| --- | --- | --- |
| Methyl palmitate (C16:0) | 10.5% | ? |
| Methyl Stearate (C18:0) | 5.7% | ? |
| Methyl Oleate (C18:1) | 25.8% | ? |
| Methyl Linoleate (C18:2) | 49.7% | ? |
| Methyl Linolenate (C18:3) | 8.3% | ? |
| Others (>C20) | Traces | ? |
| Total saturated fatty acids | 16.2% | ? |

The cloud point of the fractionated SME was −40.2° C.

EXAMPLE 3

20 grams of Soy Methyl Esters and 2 g of urea were added to 30 ml of methanol. The mixture was heated to ~40° C., with constant stirring in a round bottom flask. After all components were dissolved, the flask was connected to a rotary evaporator and the methanol was evaporated applying ~20 in Hg of vacuum and a water bath at 60° C. 50 ml of hexane were added to the residual contents of the flask and the contents of the flask were shaken for 2-3 minutes and then transferred into a Buchner funnel. The hexane extract was recovered by vacuum filtration, transferred into a round bottom flask and connected to a rotary evaporator to flash off the hexane and thus recover the unsaturated-rich soy methyl esters. The yield was 92.1% of the initial SME mass. The FAE profile of the material before and after treatment is shown in Table 6.

TABLE 6

| Fatty acid methyl ester | Original SME Composition | Fractionated SME composition |
| --- | --- | --- |
| Methyl palmitate (C16:0) | 10.5% | 8.9% |
| Methyl Stearate (C18:0) | 5.7% | 4.8% |
| Methyl Oleate (C18:1) | 25.8% | 24.1% |
| Methyl Linoleate (C18:2) | 49.7% | 54.9% |
| Methyl Linolenate (C18:3) | 8.3% | 7.3% |
| Others (>C20) | Traces | Traces |
| Total saturated fatty acids | 16.2% | 13.7% |

The cloud point of the fractionated SME was −4.5° C.

EXAMPLE 4

20 grams of Soy Methyl Esters and 4 g of urea were added to 30 ml of methanol. The mixture was heated to ~60° C., with constant stifling in a round bottom flask. After all components were dissolved, the flask was connected to a rotary evaporator and the methanol was evaporated applying ~20 in Hg of vacuum and a water bath at 60° C. 50 ml of hexane were added to the residual contents of the flask and the contents of the flask were shaken for 2-3 minutes and then transferred into a Buchner funnel. The hexane extract was recovered by vacuum filtration, transferred into a round bottom flask and connected to a rotary evaporator to flash off the hexane and thus recover the unsaturated-rich soy methyl esters. The yield was 84.5% of the initial SME mass. The FAE profile of the material before and after treatment is shown in Table 7.

TABLE 7

| Fatty acid methyl ester | Original SME Composition | Fractionated SME composition |
| --- | --- | --- |
| Methyl palmitate (C16:0) | 10.5% | 7.6% |
| Methyl Stearate (C18:0) | 5.7% | 4.0% |
| Methyl Oleate (C18:1) | 25.8% | 24.1% |
| Methyl Linoleate (C18:2) | 49.7% | 57.0% |
| Methyl Linolenate (C18:3) | 8.3% | 7.3% |
| Others (>C20) | Traces | Traces |
| Total saturated fatty acids | 16.2% | 11.6% |

The cloud point of the fractionated SME was −6.9° C.

EXAMPLE 5

20 grams of Soy Methyl Esters and 8 g of urea were added to 45 ml of methanol. The mixture was heated to ~60° C., with constant stifling in a round bottom flask. After all components were dissolved, the flask was connected to a rotary evaporator and the methanol was evaporated applying ~20 in Hg of vacuum and a water bath at 60° C. 50 ml of hexane were added to the residual contents of the flask and the contents of the flask were shaken for 2-3 minutes and then transferred into a Buchner funnel. The hexane extract was recovered by vacuum filtration, transferred into a round bottom flask and connected to a rotary evaporator to flash off the hexane and thus recover the unsaturated-rich soy methyl esters. The yield was 84.7% of the initial SME mass. The FAE profile of the material before and after treatment is shown in Table 8.

TABLE 8

| Fatty acid methyl ester | Original SME Composition | Fractionated SME composition |
| --- | --- | --- |
| Methyl palmitate (C16:0) | 10.5% | 5.8% |
| Methyl Stearate (C18:0) | 5.7% | 1.5% |

TABLE 8-continued

| Fatty acid methyl ester | Original SME Composition | Fractionated SME composition |
|---|---|---|
| Methyl Oleate (C18:1) | 25.8% | 25.5% |
| Methyl Linoleate (C18:2) | 49.7% | 58.7% |
| Methyl Linolenate (C18:3) | 8.3% | 8.5% |
| Others (>C20) | Traces | Traces |
| Total saturated fatty acids | 16.2% | 7.4% |

The cloud point of the fractionated SME was −12.7° C.

EXAMPLE 6

First step: 50 grams of Used Cooking Oil (UCO) Methyl Esters (see composition below) and 20 g of urea were added to 125 ml of methanol. The mixture was heated to ~55° C., with constant stirring in a round bottom flask. After all components were dissolved, the flask was connected to a rotary evaporator and the methanol was evaporated applying ~20 in Hg of vacuum and a water bath at 60° C. The unsaturated UCO methyl esters were recovered by vacuum filtration. The yield for the first step was 68.1%

Second step: 20 g of the fractionated methyl esters from the first step were used for a second fractionation by adding 18 g of urea and 80 ml of methanol. The same procedure as for the first step was followed to perform a second fractionation. The yield for the second step fractionation was 38.6% of the initial UCO methyl esters masses. The FAE profile of the material before and after treatment is shown in Table 9.

TABLE 9

| Fatty acid methyl ester | Original UCO Composition | First Step - composition | Second Step- composition |
|---|---|---|---|
| C14:0 | 1.2% | 1.4% | 0.7% |
| Methyl palmitate (C16:0) | 22.5% | 17.1% | 5.6% |
| Methyl Stearate (C18:0) | 10.7% | 7.2% | 0.7% |
| Methyl Oleate (C18:1) | 46.8% | 52.0% | 63.3% |
| Methyl Linoleate (C18:2) | 16.7% | 19.2% | 25.8% |
| Methyl Linolenate (C18:3) | 1.2% | 1.1% | 1.7% |
| C20:0 | 0.1% | 1.3 | 1.2% |
| Others (>C20) | 0.7% | 0.8 | 1.0% |
| Total saturated fatty acids | 35.3% | 27.7% | 9.1% |

EXAMPLE 7

First step: 50 grams of Palm Oil Methyl Esters (PME; see composition below) and 35 g of urea were added to 250 ml of methanol. The mixture was heated to ~55 C, with constant stirring in a round bottom flask. After all components were dissolved, the mixture was cooled down to 25° C. in a water bath; the urea clathrates formed were separated by filtration. The methanol from the filtrate was removed by flash evaporation. A total of 30.5 g of PME was recovered in the filtrate (a 61% yield).

Second step: The fractionated PME recovered from the first step were used for a second fractionation by adding 25 g of urea and 250 ml of methanol. The same procedure as for the first step was followed to perform a second fractionation. The yield for the second step fractionation was 40% of the initial PME methyl esters masses.

Third step: The fractionated PME recovered from the second step were used for a third fractionation by adding 20 g of urea and 250 ml of methanol. The same procedure as for the first step was followed to perform a third fractionation. The yield for the third step fractionation was 18% of the initial PME methyl esters masses. The FAE profile of the material before and after treatment is shown in Table 10.

TABLE 10

| Fatty acid methyl ester | Original PME Composition | First Step - composition | Second Step- composition | Third step - composition |
|---|---|---|---|---|
| Methyl palmitate (C16:0) | 33.9% | 34.0% | 22.1% | 2.6% |
| Methyl Stearate (C18:0) | 6.5% | 4.6% | 1.3% | 0% |
| Methyl Oleate (C18:1) | 45.9% | 48.9% | 58.7% | 71.6% |
| Methyl Linoleate (C18:2) | 13.7% | 12.5% | 17.9% | 25.8% |
| Methyl Linolenate (C18:3) | 0% | 0% | 0% | 0% |
| C20:0 | 0% | 0% | 0% | 0% |
| Others (>C20) | 0% | 0% | 0% | 0% |
| Total saturated fatty acids | 40.4% | 27.7% | 23.4% | 2.6% |

It is envisioned that experimental results correlating C.P. to starting material using different starting material can be provided to a mathematical analysis package, e.g., SAS, for the purpose of fitting a curve to the experimental results. Such a mathematical analysis package can perform a regression analysis and provide a formula relating C.P. to molar or weight fraction of the constituents of a starting material. Such a formula will advantageously provide an analytical tool for predicting C.P. of a particular mixture by knowing the species of a fatty acid profile that make up the mixture. For example, by knowing the molar or weight fractions of C16:0, C18:0, C18:1, C18:2 and C18:3 of a particular mixture, a corresponding C.P. can be calculated.

It is also envisioned that experimental results correlating a particular starting material to the amount of urea can be provided to a mathematical analysis package, e.g., SAS, for the purpose of fitting a curve to the experimental results. Such a mathematical analysis package can perform a regression analysis and provide a formula relating the amount of urea needed compared to the known starting material to achieve a particular C.P.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of lowering the cloud point of fatty acid esters, comprising:
   (a) providing fatty acid esters;
   (b) adding solvent to the fatty acid esters;
   (c) adding urea to the fatty acid esters;
   (d) mixing the fatty acid esters, solvent and urea;
   (e) evaporating the solvent, thereby forming a clathrate-liquid mixture, wherein substantially all of the urea added in step (c) is used to form clathrates; and
   (f) separating the clathrates from the liquid in the mixture formed in step (e), thereby forming refined fatty acid esters having a lower cloud point than that of the fatty acid esters provided in step (a).

2. The method of claim 1, wherein the method takes place along a conduit, wherein steps (a), (b) and (c) comprise adding the fatty acid esters, the solvent and the urea to the conduit, respectively.

3. The method of claim 2, wherein the fatty acid esters are added to the conduit prior to the adding of the urea and solvent to the conduit.

4. The method of claim 3, wherein urea and solvent are added to the conduit together through a common inlet.

5. The method of claim 1, wherein step (e) is performed after steps (b)-(c).

6. The method of claim 5, wherein step (f) comprises feeding the clathrate-liquid mixture to a filter.

7. The method of claim 1, wherein steps (b)-(f) are repeated multiple times.

8. The method of claim 7, wherein steps (a)-(f) are performed in sequence.

9. The method of claim 7, wherein the cloud point of the refined fatty acid esters produced in step (f) is reduced each time steps (b)-(f) are repeated.

10. The method of claim 7, further comprising reusing in step (b) at least some of the evaporated solvent obtained from step (e).

11. The method of claim 1, wherein step (e) comprises evaporating substantially all of the solvent.

12. The method of claim 1, wherein step (f) comprises separating substantially all of the clathrates from the liquid in the mixture formed in step (e).

13. The method of claim 1, further comprising processing the clathrates obtained from step (f) by separating the urea from saturate enriched fatty acid esters.

14. The method of claim 13, wherein the step of separating the urea from fatty acid esters that are enriched in saturated fatty acid esters comprises:
   washing the clathrates with heated water to form a first layer of fatty acid esters and a second layer of urea dissolved in the heated water;
   separating the second layer of the urea dissolved in the heated water; and
   drying the urea.

15. The method of claim 13, further comprising:
   mixing the clathrates with a urea separation solvent in which urea does not significantly dissolve to form a first layer of fatty acid esters mixed with the urea separation solvent and a second layer of urea;
   separating the second layer of the urea from the first layer; and
   drying the urea.

16. The method of claim 15, wherein the urea separation solvent is hexane.

17. The method of claim 13, wherein the separated urea is reused in step (c).

18. A method of lowering the cloud point of fatty acid esters, comprising:
   providing a mixture including urea, fatty acid esters and a volatile solvent which dissolves urea;
   drawing a vacuum that removes the volatile solvent from the mixture and thereby increases the effective concentration of urea in the mixture;
   using substantially all of the urea in the mixture to form clathrates; and
   separating the clathrates and saturate rich esters from the liquid comprised substantially of cold flow esters.

19. The method of claim 18, wherein the step of drawing a vacuum removes substantially all of the volatile solvent.

20. The method of claim 18, wherein the step of separating clathrates comprises separating substantially all of the clathrates from the liquid.

21. The method of any of claim 18, further comprising processing the clathrates into separate components of urea and saturate enriched fatty acid esters.

* * * * *